US00PP08342P

United States Patent [19]

Meilland

[11] Patent Number: Plant 8,342

[45] Date of Patent: Aug. 10, 1993

[54] ROSE PLANT — MEIDALNU VARIETY

[75] Inventor: Alain A. Meilland, Antibes, France

[73] Assignee: The Conard-Pyle Company, West Grove, Pa.

[21] Appl. No.: 848,200

[22] Filed: Mar. 10, 1992

[51] Int. Cl.[5] ..... A01H 5/00
[52] U.S. Cl. ..... Plt./19
[58] Field of Search ..... Plt./11, 18, 19, 20

[56] References Cited

U.S. PATENT DOCUMENTS

P.P. 4,013 7/1977 De Witte ..... Plt. 19

*Primary Examiner*—Howard J. Locker
*Attorney, Agent, or Firm*—Burns, Daone, Swecker & Mathis

[57] ABSTRACT

A new and distinct variety of Hybrid Tea rose plant is provided which abundantly forms attractive fully double blossoms which are light Rose Bengal suffused with light Cherry Red in coloration. The plant exhibits a upright growth habit, forms vigorous vegation, and is well suited for cut flower production under greenhouse conditions. An excellent capacity to be forced in the greenhouse is exhibited. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Bridal Pink variety (U.S. Plant Pat. No. 2,851). The male parent (i.e., the pollen parent) was the Royalty variety (U.S. Plant Pat. No. 4,057). The parentage of the new variety can be summarized as follows:

Bridal Pink×Royalty.

The seeds resulting from the above pollination were sown and 11 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long lasting fully double blossoms having an elegant configuration when opening in a vase which are light Rose Bengal suffused with light Cherry Red,
(b) exhibits vigorous vegetation,
(c) exhibits an upright growth habit,
(d) is particularly suited for cut flower production and exhibits an excellent capacity to be forced in a greenhouse, and
(e) is not particularly affected by cryptogamic diseases.

The new variety well meets the needs of the horticultural industry and is particularly well suited for use as in the production of distinctive cut flowers.

The new variety has been found to undergo asexual propagation in France and in the United States by a number of routes, including budding, grafting, cuttage, etc. The characteristics of the new variety have been found to be strictly transmissible by such asexual propagation from one generation to another.

The new variety has been named the Meidalnu variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during October while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
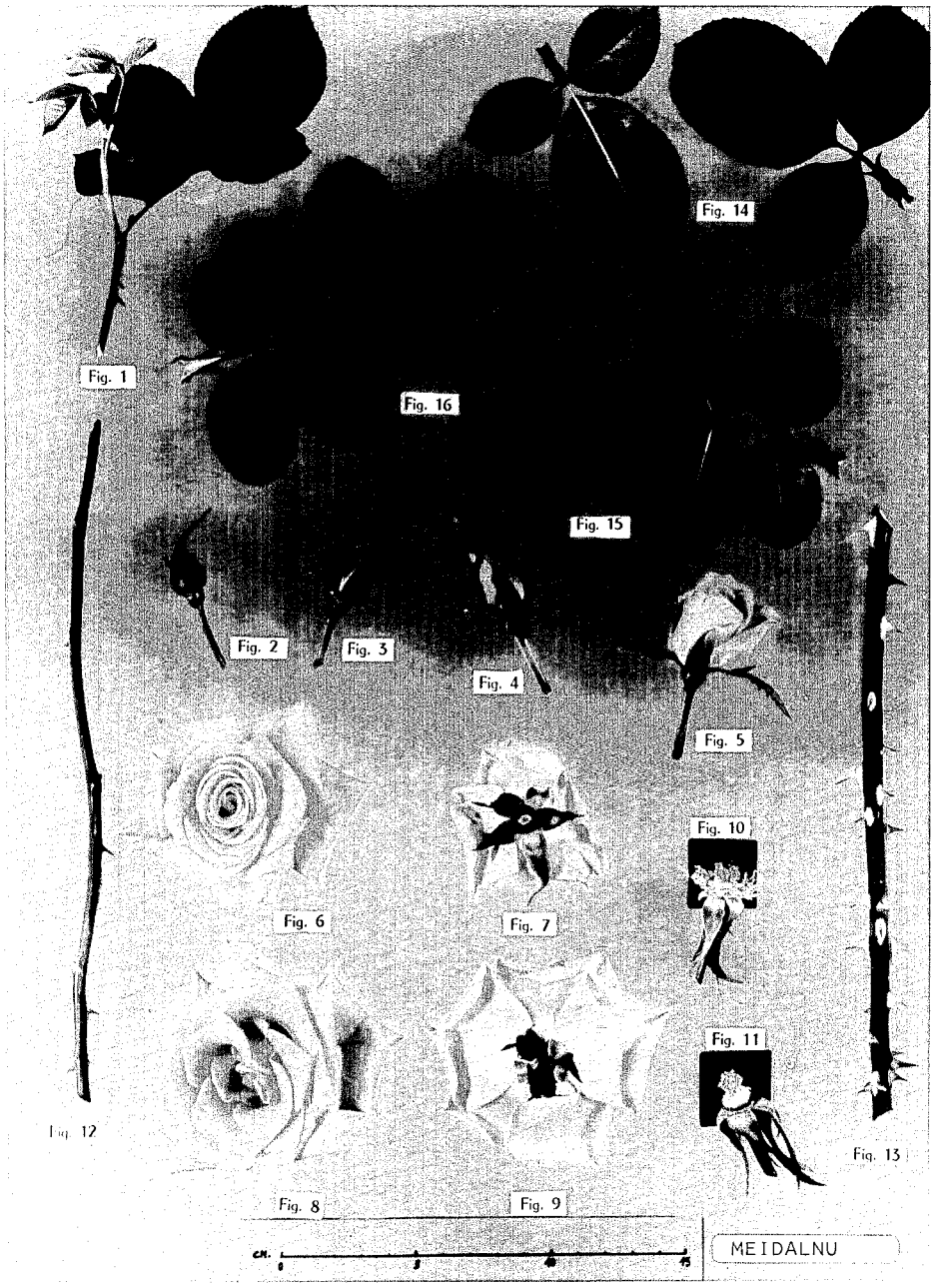
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptable showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — plan view — upper surface (right) and lower surface (left)
FIG. 15 illustrates a specimen of a leaf with five leaflets — plan view — lower surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of one year old plants made during October while budded on *Rosa indica* understock and growing in greenhouses at Cap d' Antibes, France. The coloration in common terms precedes reference to the chart.

Class: Hybrid Tea.

Plant:

*Height.*—When the plants are cut to a height of 85 cm., flowering stems are produced having a length of approximately 40 to 70 cm. When grown outdoors at Wasco, Calif., the plants commonly reach a height of approximately 120 cm. at the end of one growing season.

*Habit.*—Upright.

Branches:

*Color.*—Young stems: medium green, Green Group 143A. Adult wood: medium green, Green Group 143B.

*Thorns.*—Size: medium. Quantity: average. Color: greenish on young stems and greenish changing to tan on mature wood.

Leaves:

*Stipules.*—Adnate, pectinate, wide and linear.

*Petioles.*—Upper surface: striped reddish brown on young foliage and medium green on adult foliage with glandular edges. Under surface: light green, and bears numerous prickles.

*Leaflets.*—Number: 3, 5 (most often), and 7. Shape: oval to rounded. Serration: single and regular. Texture: leathery. General appearance: dense, bright foliage. Color (young foliage): Upper surface: medium green, Green Group 143A, more or less stained with reddish coloration. Under surface: light green, Green Group 143C, more or less stained with reddish coloration. Color (adult foliage): Upper surface: medium green, Green Group 137B. Under surface: light green, Green Group 137C.

Inflorescence:

*Number of flowers.*—Usually one single bloom per stem.

*Peduncle.*—Light green and bears numerous prickles and glandular acicules. The length is approximately 10 to 11 cm. on average.

*Sepals.*—Upper surface: tomentose, greenish in coloration. Under surface: light green and the outer sepals have only slightly appenduculated edges.

*Buds.*—Shape: conical. Length: approximately 3 cm. on average. Size: medium. Color upon opening: Upper surface: light Rose Bengal, Red-Purple Group 57C, and more or less suffused with light Cherry Red, Red Group 45C. Under surface: light Rose Bengal, Red-Purple Group 57D, and more or less suffused with light Cherry Red, Red Group 45C.

*Flower.*—Shape: cup-like with parallel sides and fully double. Diameter: approximately 8 to 10 cm. on average. Color (when opening begins): Upper surface: light Rose Bengal, Red-Purple Group 57C, more or less suffused with light Cherry Red, Red Group 45C. Under surface: light Rose Bengal, Red-Purple Group 57D, more or less suffused with light Cherry Red, Red Group 45C. Color (when blooming): Upper surface: light Rose Bengal, Red-Purple Group 57C, more or less suffused with light Cherry Red, Red Group 45C. Under surface: light Rose Bengal, Red-Purple Group 57D, more or less suffused with light Cherry Red, Red Group 45C. Color (at end of opening): Upper surface: light Rose Bengal, Red-Purple Group 57C, more or less suffused with light Cherry Red, Red Group 45C. Under surface: light Rose Bengal, Red-Purple Group 57D, more or less suffused with light Cherry Red, Red Group 45C. Fragrance: none. Lasting quality: average. Petal number: approximately 25 to 26 on average. Petal shape: rounded to oval with reflective lateral sides. Texture: consistent. Petal drop: good. Stamen number: approximately 191 on average. Anthers: yellowish in coloration. Filaments: irregular in height, and dark fuschia in coloration. Pistils: approximately 135 on average. Stigmas: ochre colored. Styles: fuschia in coloration, and very tomentose at base. Receptacle: light green in coloration, smooth, and in longitudinal section at the dehiscence of the anthers it is in the shape of a pitcher.

Development:

*Vegetation.*—Vigorous.

*Blooming.*—Abundant.

*Resistance to diseases.*—Good.

*Aptitude to be forced.*—Excellent.

I claim:

1. A new and distinct variety of Hybrid Tea rose plant characterized by the following combination of characteritics:

(a) forms in abundance attractive long lasting fully double blossoms having an elegant configuration when opening in a vase which are light Rose Bengal suffused with light Cherry Red,
(b) exhibits vigorous vegetation,
(c) exhibits an upright growth habit,
(d) is particularly suited for cut flower production and exhibits an excellent capacity to be forced in a greenhouse, and
(e) is not particularly affected by cryptogamic diseases;

substantially as herein shown and described.

* * * * *

CM.
0
5
10
15
MEIDALNU